(12) United States Patent
Crucs et al.

(10) Patent No.: US 8,184,147 B2
(45) Date of Patent: May 22, 2012

(54) APPARATUS AND METHODS FOR FULL-MOUTH INTRAORAL IMAGE ACQUISITION

(76) Inventors: Kevin Crucs, Copley, OH (US); Angela Daetwyler, Ravenna, OH (US)

( * ) Notice: Subject to any disclaimer, the term of this patent is extended or adjusted under 35 U.S.C. 154(b) by 971 days.

(21) Appl. No.: 12/178,734

(22) Filed: Jul. 24, 2008

(65) Prior Publication Data

US 2010/0020165 A1    Jan. 28, 2010

(51) Int. Cl.
*A61B 1/04* (2006.01)
(52) U.S. Cl. ............................................. 348/66; 396/16
(58) Field of Classification Search .................... 348/66; 396/16
See application file for complete search history.

(56) References Cited

U.S. PATENT DOCUMENTS

| | | | | |
|---|---|---|---|---|
| 4,945,367 A * | 7/1990 | Blackshear | .................. | 348/143 |
| 5,023,725 A * | 6/1991 | McCutchen | .................. | 348/38 |
| 5,027,138 A * | 6/1991 | Gandrud | .................. | 348/66 |
| 5,528,432 A * | 6/1996 | Donahoo | .................. | 348/66 |
| 5,766,006 A * | 6/1998 | Murljacic | .................. | 433/26 |
| 5,901,252 A * | 5/1999 | Kawakami et al. | .................. | 348/442 |
| 6,002,430 A * | 12/1999 | McCall et al. | .................. | 348/36 |
| 6,123,437 A | 9/2000 | Holmes | | |
| 6,169,781 B1 | 1/2001 | Doebert et al. | | |
| 6,201,880 B1 * | 3/2001 | Elbaum et al. | .................. | 348/66 |
| 6,338,627 B2 * | 1/2002 | Hirsch et al. | .................. | 433/93 |
| 6,587,189 B1 | 7/2003 | Roberts et al. | | |
| 7,106,958 B2 * | 9/2006 | Kerschbaumer et al. | ....... | 348/66 |
| 7,336,763 B2 | 2/2008 | Spartiotis et al. | | |
| 7,676,022 B2 | 3/2010 | Pantsar et al. | | |
| 2005/0026104 A1 | 2/2005 | Takahashi | | |
| 2006/0166162 A1 | 7/2006 | Ting | | |
| 2008/0096154 A1 | 4/2008 | Rakocz | | |

FOREIGN PATENT DOCUMENTS

| | | |
|---|---|---|
| EP | 0 282 832 | 3/1988 |
| JP | 2001212081 | 8/2001 |
| WO | 2007063980 | 6/2007 |

\* cited by examiner

*Primary Examiner* — Ajay Bhatia
(74) *Attorney, Agent, or Firm* — Hahn Loeser & Parks LLP (57) ABSTRACT

Apparatus and methods for full-mouth intraoral image acquisition. An intraoral sensor configuration includes a multi-aperture digital camera and/or a conformal layered sensor structure, a bite piece, and an electronic cable for imaging inside surfaces of a mouth of a patient without having to re-position the digital camera and/or the conformal layered sensor structure within the mouth of the patient during an image acquisition session. Images may be acquired sequentially or simultaneously.

25 Claims, 11 Drawing Sheets

APPARATUS AND METHODS FOR FULL-MOUTH INTRAORAL IMAGE ACQUISITION

TECHNICAL FIELD

Certain embodiments of the present invention relate to intraoral imaging. More particularly, certain embodiments relate to sensor configurations and methods for full-mouth intraoral image acquisition.

BACKGROUND

When a patient goes to a doctor's office, images of the inside of the patient's mouth are sometimes acquired (e.g., visible light images using a visible light camera) in order to look at bad areas of teeth or abnormal growths, for example. Often, many images are acquired and the imaging sensor is re-positioned within the patient's mouth multiple times in order to acquire all of the images. Such multiple re-positionings of an image sensor and corresponding image acquisitions can take a long time and can increase the chances of unsanitary conditions occurring in the patient's mouth.

Further limitations and disadvantages of conventional, traditional, and proposed approaches will become apparent to one of skill in the art, through comparison of such approaches with the subject matter of the present application as set forth in the remainder of the present application with reference to the drawings.

SUMMARY

An embodiment of the present invention comprises an intraoral sensor configuration. The configuration includes a multi-aperture digital camera having a generally spherical shape and being of a size to fit in a mouth of a patient to image inside surfaces of the mouth of the patient over a generally spherical field-of-view while remaining in a fixed position within the mouth. The configuration also includes a bite piece attached to the generally spherical multi-aperture digital camera at a distal end of the bite piece. The configuration further includes an electronic cable positioned through the bite piece (e.g., if the bite piece is hollow) and having a distal end thereof operatively coupled internally to the generally spherical multi-aperture digital camera. The cable provides a transmission path for transmitting digital image data formed by the multi-aperture digital camera out of the multi-aperture digital camera through the bite piece.

The multi-aperture digital camera may include a plurality of optical apertures arranged in a generally spherical configuration and a plurality of illumination sources arranged between the plurality of optical apertures. The plurality of optical apertures may each include one of a wide-angle optical lens, an optical fiber, and an optical fiber bundle. The plurality of illumination sources may each include one of a light emitting diode, a laser diode, a light emitting diode optically coupled to at least one optical fiber, and a laser diode optically coupled to at least one optical fiber.

The multi-aperture digital camera may further include a plurality of sensor arrays, one sensor array arranged behind each of the optical apertures, capable of capturing electromagnetic energy passing through the optical apertures and converting the captured electromagnetic energy to electrical signals. The electromagnetic energy may include at least one of visible light energy, ultraviolet energy, and infrared energy. Each of the sensor arrays may include one of a charge-coupled device (CCD), a solid state device, an active pixel sensor array, and a complementary metal oxide semiconductor (CMOS) array.

The multi-aperture digital camera may also include a digital memory and a first control circuitry capable of reading out the electrical signals from the plurality of sensor arrays and storing a representation of the electrical signals to the digital memory as pixels of the digital image data. The multi-aperture digital camera may further include a second control circuitry capable of reading out the digital image data from the digital memory and transmitting the digital image data over the electronic cable.

As an alternative, the multi-aperture digital camera may include a plurality of optical apertures arranged in a generally spherical configuration, a plurality of illumination sources arranged between or among the plurality of optical apertures, a single movable sensor array movably mounted within the generally spherical configuration of optical apertures and capable of capturing electromagnetic energy passing through the optical apertures and converting the captured electromagnetic energy to electrical signals as the single movable sensor array moves, a digital memory, first control circuitry capable of reading out the electrical signals from the single movable sensor array and storing a representation of the electrical signals to the digital memory as pixels of the digital image data, and second control circuitry capable of reading out the digital image data from the digital memory and transmitting the digital image data over the electronic cable.

The multi-aperture digital camera may further include an internal power source capable of providing power to at least one of the plurality of illumination sources, the plurality of sensor arrays, the digital memory, the first control circuitry, and the second control circuitry. The internal power source may include a battery. As an alternative, the multi-aperture digital camera may use an external power source capable of providing power to at least one of the plurality of illumination sources, the plurality of sensor arrays, the digital memory, the first control circuitry, and the second control circuitry via the electronic cable. The external power source may include a power supply.

The second control circuitry may be capable of reading out and transmitting the digital image data in a serial manner, in a parallel manner, or some segmented combination thereof. An electrical connector may be operatively coupled at a proximal end of the electronic cable. As an alternative, a radio frequency antenna may be operatively coupled at a proximal end of the electronic cable. The cable may be further capable of providing a transmission path for transmitting control signals from an image processor to the multi-aperture digital camera through the bite piece. During an image acquisition process, the plurality of sensor arrays may be capable of capturing electromagnetic energy one sensor array at a time or all at the same time.

Another embodiment of the present invention comprises an intraoral sensor configuration. The configuration includes an optical fiber layer and a plurality of illumination sources interspersed throughout the optical fiber layer. Each of the plurality of illumination sources may include one of a light emitting diode, a laser diode, a light emitting diode optically coupled to at least one optical fiber, and a laser diode optically coupled to at least one optical fiber.

The configuration further includes a sensor layer optically coupled to the optical fiber layer and capable of capturing electromagnetic energy passing through the optical fiber layer. The electromagnetic energy may include at least one of visible light energy, ultraviolet energy, and infrared energy. The configuration also includes an electronic cable operatively coupled to the sensor layer and providing a transmission path for transmitting digital image data formed by the sensor layer out of the sensor layer.

The sensor layer may include a pixel sensor array capable of converting the captured electromagnetic energy to electrical signals, a digital memory, and a control circuitry capable of reading out the electrical signals from the pixel sensor array and storing a representation of the electrical signals to the digital memory as pixels of the digital image data. The control circuitry may also be capable of reading out the digital image data from the digital memory and transmitting the digital image data over the electronic cable. The control circuitry may be capable of reading out and transmitting the digital image data in one of a serial manner, a parallel manner, or some segmented combination thereof.

The sensor layer may include a pixel sensor array capable of converting the captured electromagnetic energy to electrical signals and a control circuitry capable of reading out the electrical signals as the digital image data from the pixel sensor array and transmitting the digital image data over the electronic cable. The electronic cable may be capable of providing a transmission path for transmitting control signals from an image processor to the sensor layer.

An electrical connector and/or a radio frequency antenna may be operatively coupled at a proximal end of the electronic cable. The configuration may further include an external power source capable of providing power to at least one of the plurality of illumination sources and the sensor layer via the electronic cable.

The configuration may also include a bite piece mechanically attached to at least the sensor layer and having the electronic cable positioned therethrough (e.g., if the bite piece is hollow). The sensor layer may include at least one of a charge-coupled device (CCD), a solid state device, an active pixel sensor array, and a complementary metal oxide semiconductor (CMOS) array.

A further embodiment of the present invention comprises an intraoral sensor configuration. The configuration includes a multi-aperture digital camera having a generally spherical shape and being of a size to fit in a mouth of a patient to image inside surfaces of the mouth of the patient over a generally spherical field-of-view while remaining in a fixed position within the mouth. The configuration further includes a bite piece attached to the generally spherical multi-aperture digital camera at a distal end of the bite piece. The configuration also includes a layered structure of optical fibers and pixel sensor arrays attached to the bite piece at a generally middle portion of the bite piece and having a conformal shape to image at least one of buccal surfaces of the mouth, occlusion surfaces of teeth within the mouth, and frontal surfaces of teeth within the mouth while remaining in a fixed position within the mouth. The configuration further includes at least one electronic cable positioned through the bite piece and being operatively coupled internally to the generally spherical multi-aperture digital camera and the layered structure. The at least one cable provides a transmission path for transmitting digital image data formed by the multi-aperture digital camera and the layered structure out of the multi-aperture digital camera and the layered structure through the bite piece.

Another embodiment of the present invention comprises a method to image inside surfaces within a mouth of a patient. The method includes positioning a generally spherical multi-aperture digital camera within a mouth of the patient and having the patient bite down on a bite piece attached to the multi-aperture digital camera. The method further includes acquiring intraoral digital image data over a full spherical field-of-view using the multi-aperture digital camera while the multi-aperture digital camera remains in a fixed position within the mouth of the patient. The method also includes transmitting the digital image data from the multi-aperture digital camera to an image acquisition machine via a transmission path through the bite piece.

A further embodiment of the present invention comprises a method to image inside surfaces within a mouth of a patient. The method includes positioning a conformal layered sensor structure within a mouth of a patient against an irregular surface of the mouth of the patient and having the patient bite down on a bite piece attached to the conformal layered sensor structure. The method further includes acquiring intraoral digital image data of the irregular surface using the conformal layered sensor structure while the conformal layered sensor structure remains in a fixed position within the mouth of the patient. The method also includes transmitting the digital image data from the conformal layered sensor structure to an image acquisition machine via a transmission path through the bite piece.

These and other novel features of the subject matter of the present application, as well as details of illustrated embodiments thereof, will be more fully understood from the following description and drawings.

DETAILED DESCRIPTION

Figure 1:
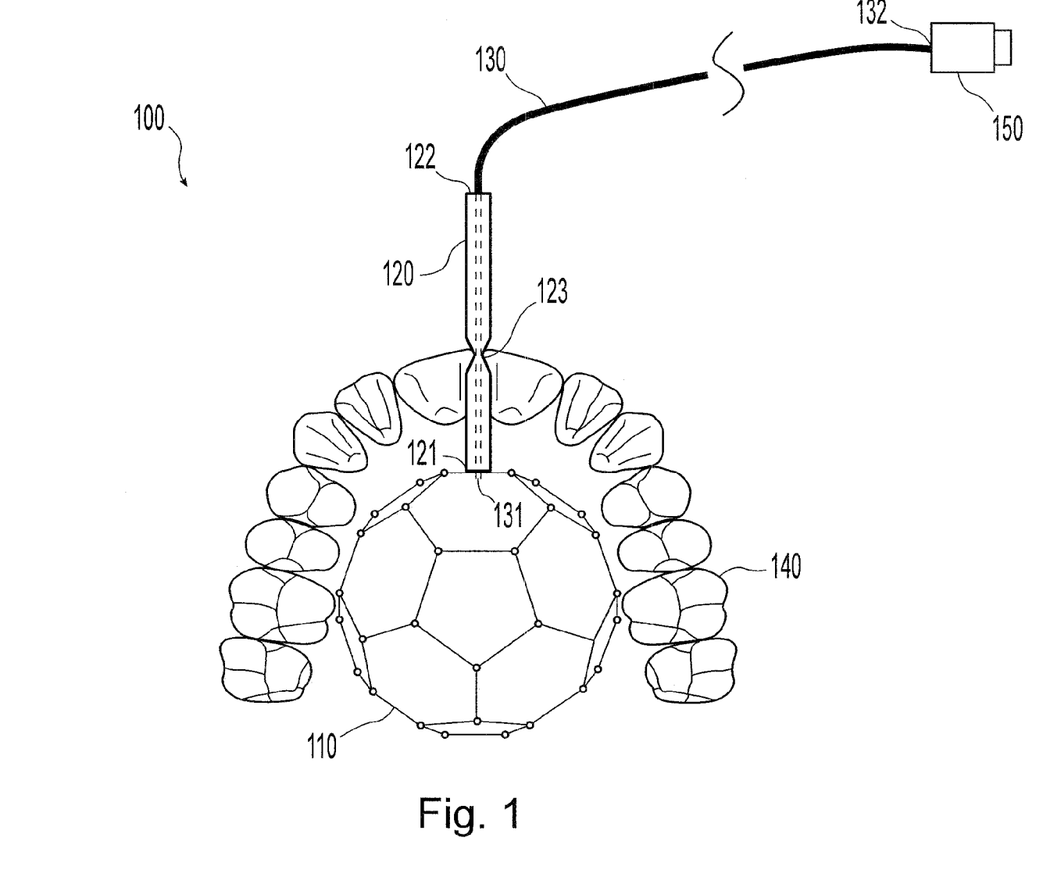
FIG. 1 illustrates a schematic diagram of a first exemplary embodiment of an intraoral sensor configuration having a multi-aperture digital camera.

FIG. 1 illustrates a schematic diagram of a first exemplary embodiment of an intraoral sensor configuration 100 having a multi-aperture digital camera 110. The intraoral sensor configuration 100 includes the multi-aperture digital camera 110, a hollow bite piece 120, and an electronic cable 130. The multi-aperture digital camera 110 has a generally spherical shape and is of a size to fit in a mouth of a patient (see in reference to the teeth 140) in order to image inside surfaces of the mouth of the patient over a generally spherical field-of-view (360 degrees around in every direction) while remaining in a fixed position within the patient's mouth. In certain embodiments, the multi-aperture digital camera 110 may be more elliptical or oblong than spherical. However, the term "generally spherical" as used herein is meant to include such elliptical or oblong shapes.

The hollow bite piece 120 is attached to the generally spherical multi-aperture digital camera at a distal end 121 of the bite piece 120. The combined bite piece 120 and digital camera 110 of the configuration 100 resemble a candy lollipop or sucker and is placed similarly in the patient's mouth. The bite piece 120 may include a notch 123 allowing a patient to bite down at the notch to securely hold the bite piece 120 and attached camera 110 in place. The multi-aperture digital camera 110 may be placed above the tongue or below the tongue for imaging corresponding portions of the patient's mouth.

The electronic cable 130 is positioned through the hollow bite piece 120. A distal end 131 of the electronic cable 130 is operatively coupled internally to the generally spherical multi-aperture digital camera 110. The cable 130 exits the bite piece 120 at a proximal end 122 of the bite piece 120. The cable 130 provides a transmission path for transmitting digital image data formed by the multi-aperture digital camera 110 out of the multi-aperture digital camera 110 through the bite piece 120. At a proximal end 132 of the cable is an electrical connector 150 that is operatively coupled to the electronic cable 130. The electrical connector 150 may be used to interface the cable 130 to, for example, an image processing machine (not shown) in order to process the digital image data to form images for display. For example, the electrical connector 150 may be a universal serial bus (USB) connector.

Figure 2:
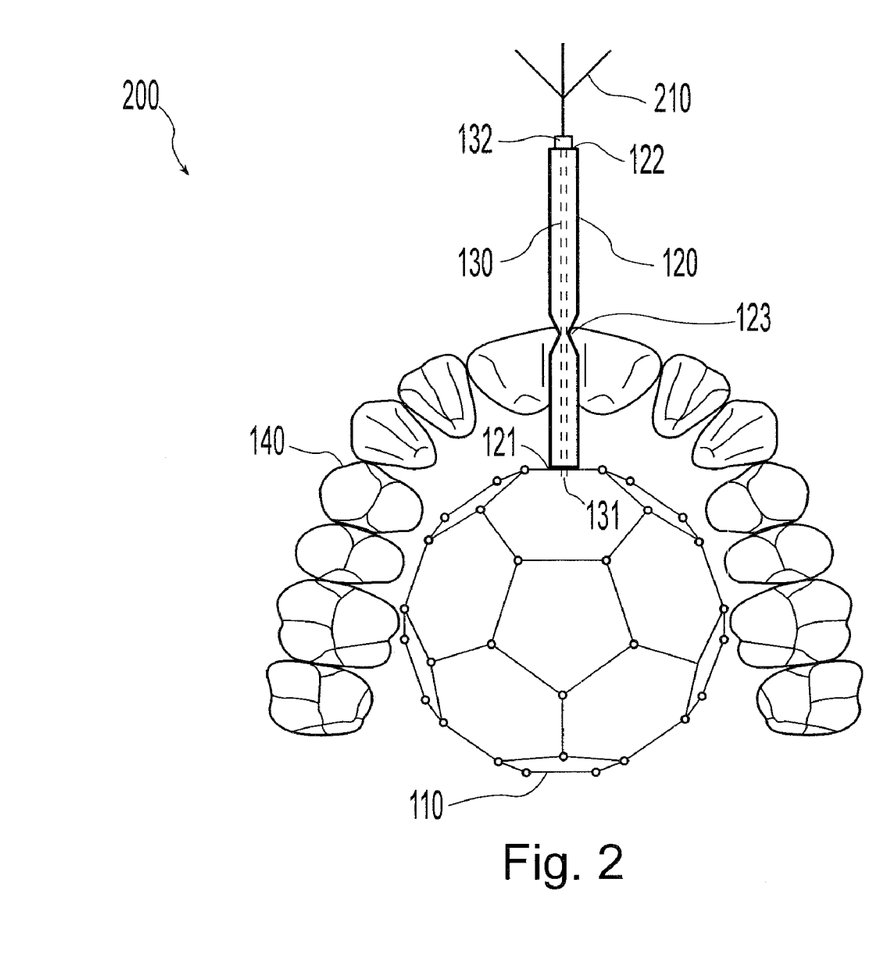
FIG. 2 illustrates a schematic diagram of a second exemplary embodiment of an intraoral sensor configuration having a multi-aperture digital camera.

FIG. 2 illustrates a schematic diagram of a second exemplary embodiment of an intraoral sensor configuration 200 having a multi-aperture digital camera 110. The configuration 200 includes the multi-aperture digital camera 110, the hollow bite piece 120, and the cable 130 as in FIG. 1. However, instead of an electrical connector 150, the configuration 200 includes a radio frequency (RF) antenna 210 operatively coupled at a proximal end 132 of the cable 130. The RF antenna 210 may be used to wirelessly transmit digital image data formed by the multi-aperture digital camera 110 to, for example, an image processing machine (not shown) in order to process the digital image data to form images for display. A wireless transmission protocol such as, for example, BLUETOOTH, may be employed.

Figure 3:
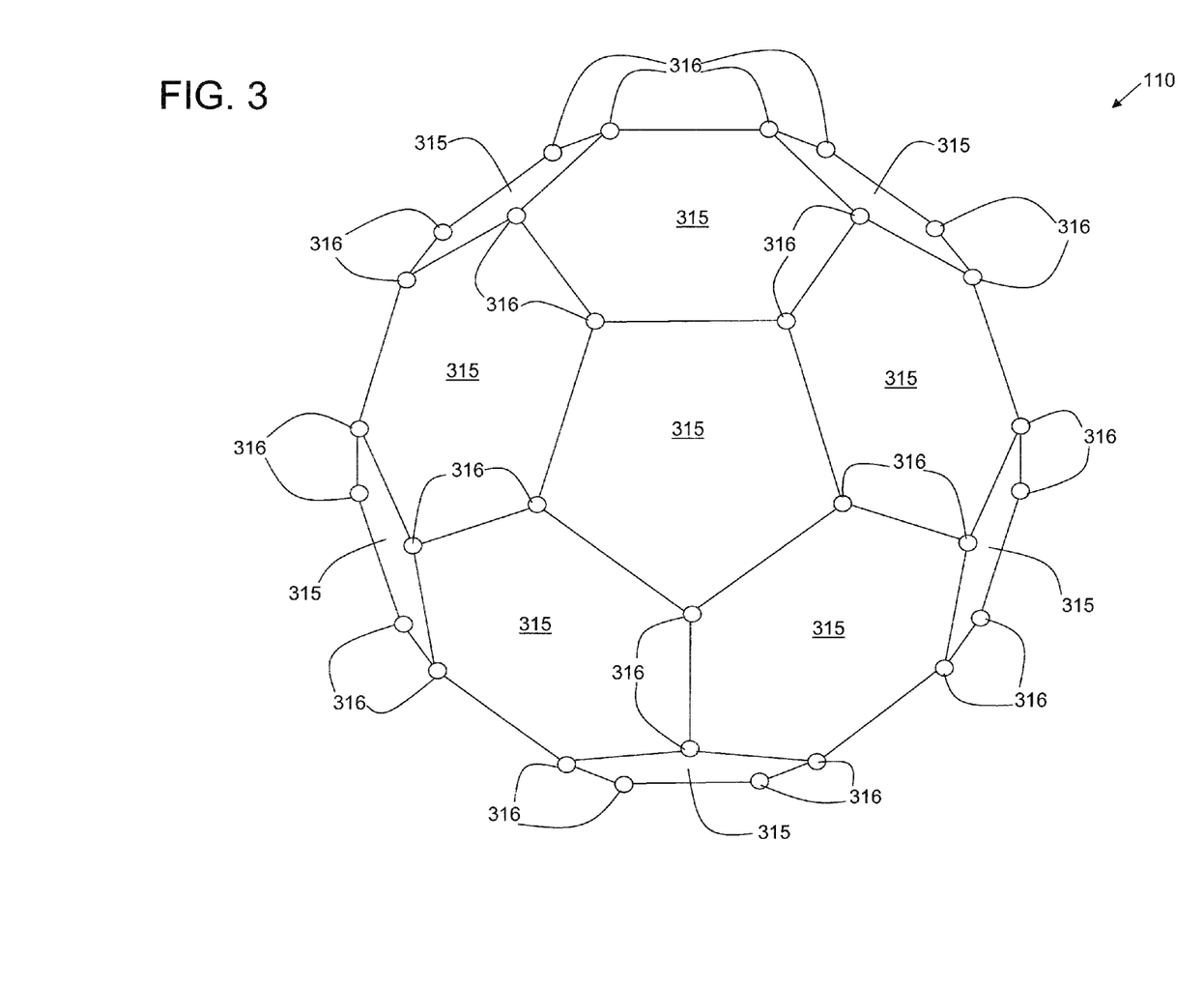
FIG. 3 illustrates a schematic diagram of a first exemplary embodiment of a multi-aperture digital camera that may be used in the intraoral sensor configuration of FIG. 1 and FIG. 2.

FIG. 3 illustrates a schematic diagram of a first exemplary embodiment of a multi-aperture digital camera 110 that may be used in the intraoral sensor configuration 100 of FIG. 1 and 200 of FIG. 2. The surface of the multi-aperture digital camera 110 is made up of a plurality of optical apertures 315. In accordance with an embodiment of the present invention, there are a total of thirty-two hexagonal and pentagonal shaped optical apertures 315 making up the surface of the multi-aperture digital camera 110. The optical apertures 315 are windows or wide-angle lenses that allow electromagnetic energy (e.g., visible light) to pass.

In between the optical apertures 315 are a plurality of illumination sources 316 (e.g., at the corners of the optical apertures 315). The illumination sources 316 are used to illuminate the inside of a patient's mouth with electromagnetic energy (e.g., visible light) such that the electromagnetic energy may reflect off of interior surfaces of the patient's mouth and back through the optical apertures 315 in order to image the interior surfaces of the patient's mouth.

Figure 4:
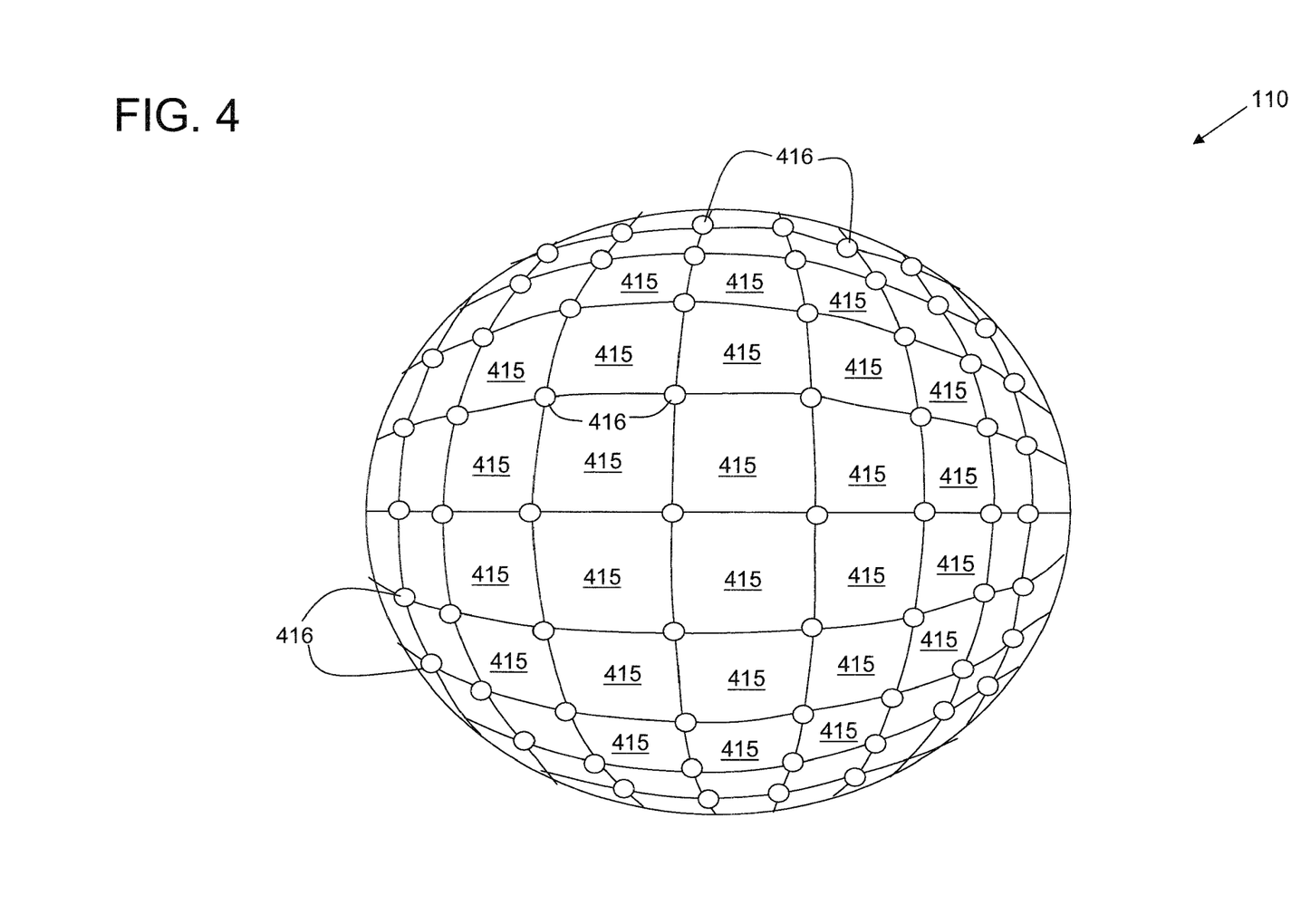
FIG. 4 illustrates a schematic diagram of a second exemplary embodiment of a multi-aperture digital camera that may be used in the intraoral sensor configuration of FIG. 1 and FIG. 2.

Similarly, FIG. 4 illustrates a schematic diagram of a second exemplary embodiment of a multi-aperture digital camera 110 that may be used in the intraoral sensor configuration 100 of FIG. 1 and 200 of FIG. 2. Again, the surface of the multi-aperture digital camera 110 is made up of a plurality of optical apertures 415. In accordance with an embodiment of the present invention, there are a plurality of curved but generally rectangularly shaped optical apertures 415 making up the surface of the multi-aperture digital camera 110. The optical apertures 415 are windows or wide-angle lenses that allow electromagnetic energy (e.g., visible light) to pass. In FIG. 4, a representative sample of optical apertures 415 are shown and labeled.

In between the optical apertures 415 are a plurality of illumination sources 416 (e.g., at the corners of the optical apertures 415). The illumination sources 416 are used to illuminate the inside of a patient's mouth with electromagnetic energy (e.g., visible light) such that the electromagnetic energy may reflect off of interior surfaces of the patient's mouth and back through the optical apertures 415 in order to image the interior surfaces of the patient's mouth. In FIG. 4, a representative sample of illumination sources 416 are shown and labeled.

Figure 5:
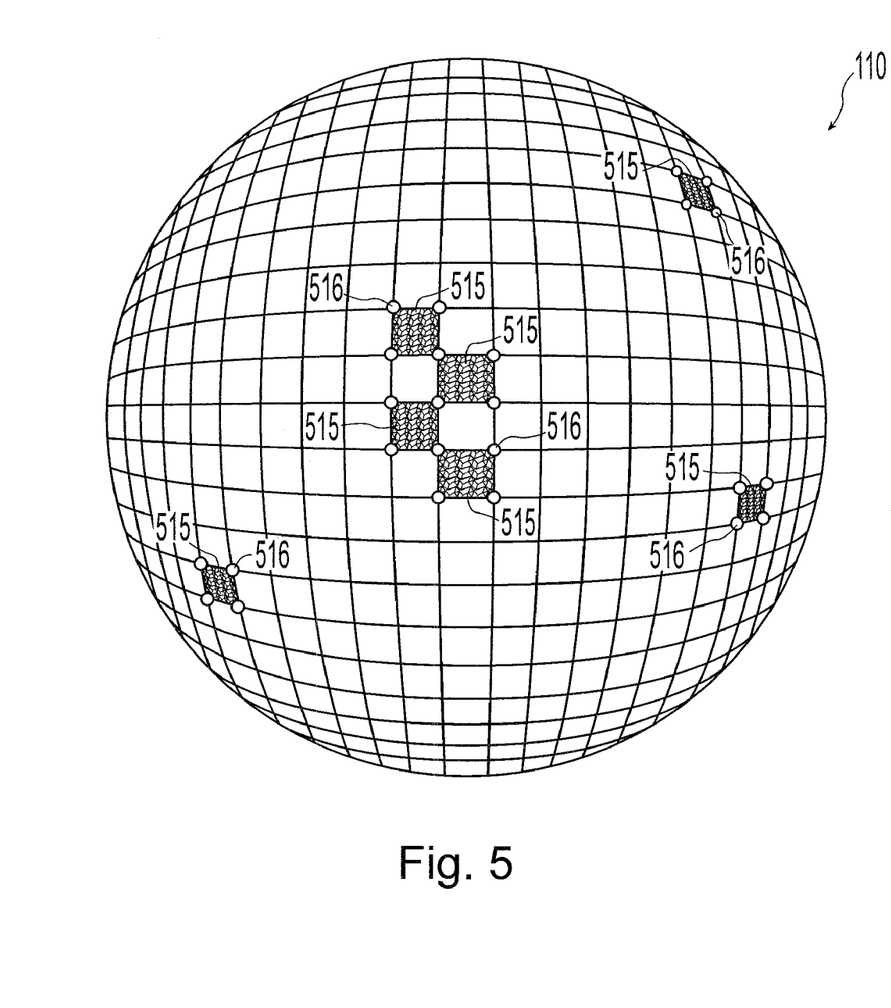
FIG. 5 illustrates a schematic diagram of a third exemplary embodiment of a multi-aperture digital camera that may be used in the intraoral sensor configuration of FIG. 1 and FIG. 2.

FIG. 5 illustrates a schematic diagram of a third exemplary embodiment of a multi-aperture digital camera 110 that may be used in the intraoral sensor configuration 100 of FIG. 1 and 200 of FIG. 2. The surface of the multi-aperture digital camera 110 is made up of a plurality of fiber optic bundles 515, each fiber optic bundle 515 being made up of a plurality of optical fibers. In accordance with an embodiment of the present invention, each fiber optic bundle 515 is generally rectangularly shaped. In FIG. 5, a representative sample of fiber optic bundles 515 are shown and labeled. Each optical fiber of each fiber optic bundle 515 couples electromagnetic energy (e.g., visible light) from the exterior of the multi-aperture digital camera 110 to the interior of the multi-aperture digital camera 110.

In between the fiber optic bundles 515 are a plurality of illumination sources 516 (e.g., at the corners of the fiber optic bundles 515). The illumination sources 516 are used to illuminate the inside of a patient's mouth with light such that the light may reflect off of interior surfaces of the patient's mouth and back to the fiber optic bundles 515 in order to image the interior surfaces of the patient's mouth. The proximal ends of each optical fiber of the fiber optic bundles 515 may be shaped (e.g., as a wide-angle lens) to maximize the coupling of light into the optical fibers. In FIG. 5, a representative sample of illumination sources 516 are shown and labeled.

Figure 6:
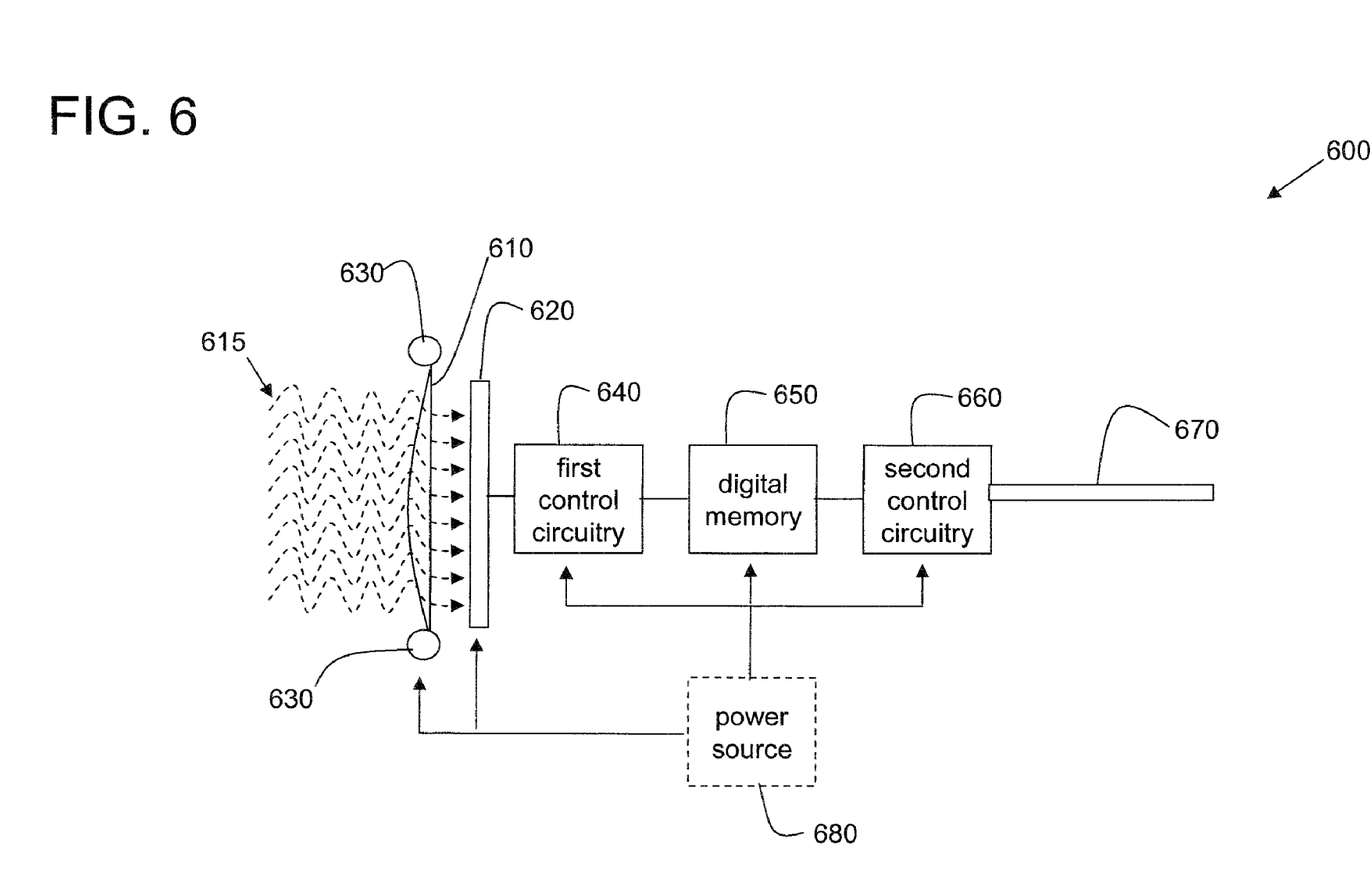
FIG. 6 illustrates a schematic block diagram of an exemplary embodiment of a portion of an intraoral sensor configuration.

FIG. 6 illustrates a schematic block diagram of an exemplary embodiment of a representative portion 600 of a multi-aperture digital camera (e.g., 110) of an intraoral sensor configuration (e.g., configuration 100 of FIG. 1 or configuration 200 of FIG. 2). The portion 600 includes an optical aperture 610 (e.g., a wide angle lens 315 or 415, or a fiber optic bundle 515) positioned in front of a sensor array 620. The portion 600 also includes illumination sources 630 (e.g., 316, 416, or 516) positioned about the optical aperture 610. The optical aperture 610 couples reflected electromagnetic energy 615 (e.g. visible light) from an internal surface of a patient's mouth to the sensor array 620. The sensor array 620 captures the electromagnetic energy 615 passing through the optical aperture 610 and impinging on the sensor array 620 and converts the electromagnetic energy 615 to electrical signals. The electromagnetic energy 615 may be one of visible light energy, ultraviolet energy, or infrared energy, for example.

The sensor array 620 may be a part of a charge-coupled-device (CCD), a solid state device, an active pixel sensor array, a CMOS array, or any other type of device capable of converting electromagnetic energy to form a plurality of pixels of representative electrical signals, as are well known in the art. The illumination sources 630 may be light emitting diodes (LEDs) or laser diodes (as are well known in the art), for example, each having a radiating lens positioned on the surface of the multi-aperture digital camera (e.g., 110) in order to illuminate a portion of a patient's mouth. As an alternative, LED's or laser diodes may be located internally within the multi-aperture digital camera 110 and the resultant light from those devices may be piped upward toward the surface of the multi-aperture digital camera 110 via optical fibers, fiber optic bundles, or light tubes for example.

The portion 600 also includes a first control circuitry 640 and a digital memory 650. The first control circuitry 640 reads out the electrical signals from the sensor array 620 and stores a representation of the electrical signals to the digital memory 650 as pixels of digital image data. The portion 600 further includes a second control circuitry 660 and an electronic data channel 670. The second control circuitry 660 reads out the digital image data from the digital memory 650 and transmits the digital image data over the electronic data channel 670. As an alternative, the first control circuitry 640 may read out the electrical signals from the sensor array 620 directly to the electronic data channel 670 as digital image data.

In accordance with an embodiment of the present invention, in a multi-aperture digital camera, there is a sensor array 620, a first control circuitry 640, a digital memory 650, a second control circuitry 660, and an electronic data channel 670 associated with each optical aperture 610. The digital image data transmitted on the electronic data channel 670 may be multiplexed onto an electronic cable (e.g., cable 130 as in FIG. 1) to exit the multi-aperture digital camera 110. In accordance with an embodiment of the present invention, the second control circuitry 660 is capable of reading out and transmitting the digital image data in a serial manner. In accordance with another embodiment of the present invention, the second control circuitry 660 is capable of reading out and transmitting the digital image data in a parallel manner.

In accordance with an alternative embodiment of the present invention, in the multi-aperture digital camera, there is a sensor array 620 and a first control circuitry 640 associated with each optical aperture 610. The digital memory 650 and the second control circuitry 660 is common to all sensor arrays 620 and first control circuitries 640. The electronic data channel 670 may then actually be an electronic cable (e.g., cable 130 as in FIG. 1) to exit the multi-aperture digital camera. Each first control circuitry 640 associated with each sensor array 620 for each optical aperture 610 reads out corresponding electrical signals to a common digital memory 650 as pixels of digital image data. The digital memory 650 may be large enough to store data from all of the sensor arrays 620 of the intraoral sensor configuration 100. Again, in accordance with an embodiment of the present invention, the second control circuitry 660 is capable of reading out and transmitting the digital image data in a serial manner. In accordance with another embodiment of the present invention, the second control circuitry 660 is capable of reading out and transmitting the digital image data in a parallel manner.

In accordance with a further alternative embodiment of the present invention, in the multi-aperture digital camera, there is a single movable sensor array and a single first control circuitry 640. There is also a single digital memory 650 and a single second control circuitry 660. The electronic data channel 670 may then actually be an electronic cable (e.g., cable 130 as in FIG. 1) to exit the multi-aperture digital camera. The movable sensor array may be driven to rotate by a servomechanism, for example, within the multi-aperture digital camera. The movable sensor array may move or rotate from aperture position to aperture position sequentially, acquiring a single set of image data from light passing through each aperture. The first control circuitry 640 associated with the movable sensor array reads out corresponding electrical signals to a common digital memory 650 as pixels of digital image data. The digital memory 650 may be large enough to store data from all of the apertures (or aperture positions) of the intraoral sensor configuration 100. Again, in accordance with an embodiment of the present invention, the second control circuitry 660 is capable of reading out and transmitting the digital image data in a serial manner. In accordance with another embodiment of the present invention, the second control circuitry 660 is capable of reading out and transmitting the digital image data in a parallel manner. The servomechanism may be controlled by control signals coming into the multi-aperture digital camera via the cable 130. In such a configuration, the generally spherical configuration of optical apertures may be substantially a single smooth globe-like structure, where any particular optical aperture on the globe-like structure is defined by a fixed field-of-view of the movable sensor array and predefined image acquisition positions of the movable sensor array.

An internal power source 680 (e.g., a battery) being internal to the multi-aperture digital camera 110 may provide electrical power to at least one of the illumination sources 630, the sensor array 620, the first control circuitry 640, the digital memory 650, and the second control circuitry 660. A single battery 680, for example, may supply the electrical power for all of the illumination sources 630, all of the sensor arrays 620, all of the digital memories 650, and all of the control circuitries 640 and 660 within the multi-aperture digital camera 110.

As an alternative, several batteries 680 may be provided internally to the multi-aperture digital camera 110, each dedicated to providing electrical power to certain components. As a further alternative, an external power source (e.g., a power supply) may provide electrical power to some or all of the components of the multi-aperture digital camera 110. For example, electrical power may be provided to all of the components of the multi-aperture digital camera 110 from the external power supply via the electronic cable 130, or electrical power may be provided to some of the components from the external power supply while other components receive electrical power from an internal power source 680.

In accordance with an embodiment of the present invention, the multi-aperture digital camera (e.g., 110) is capable of capturing electromagnetic energy one sensor array 620 at a time. In accordance with another embodiment of the present invention, the plurality of sensor arrays 620 are capable of capturing electromagnetic energy all at the same time. The cable 130, is further capable of providing a transmission path for transmitting control signals from, for example, an image processor or image acquisition machine to the multi-aperture digital camera 110. For example, control signals may enter a particular portion 600 of the multi-aperture digital camera 110 from the cable 130 such that the portion 600 may be triggered to acquire image data.

Figure 7:
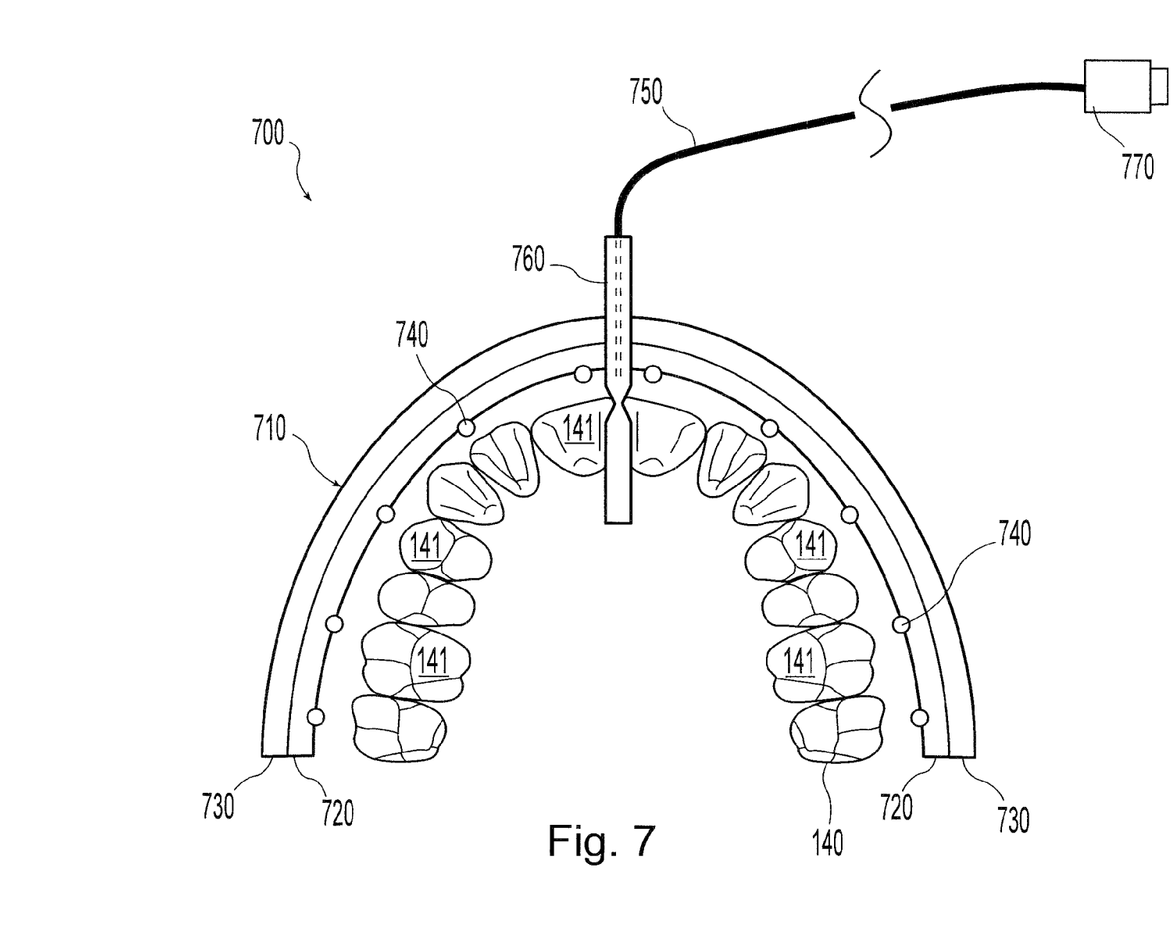
FIG. 7 illustrates a schematic diagram of a third exemplary embodiment of an intraoral sensor configuration having a conformal layered sensor structure.

FIG. 7 illustrates a schematic diagram of a third exemplary embodiment of an intraoral sensor configuration 700 having a conformal layered structure 710. The conformal layered structure 710 includes an optical fiber layer 720 and a sensor layer 730. The optical fiber layer 720 may be constructed from a plurality of optical fibers. The sensor layer 730 is optically coupled to the optical fiber layer and is capable of capturing electromagnetic energy passing through the optical fiber layer 720. Again, the electromagnetic energy may comprise, for example, visible light energy, ultraviolet energy, or infrared energy. In the configuration 700 of FIG. 7, the conformal layered structure 710 is positioned between the teeth 140 and the cheeks (not shown) of the patient.

In the configuration 700 of FIG. 7, the optical fiber layer 720 and the sensor layer 730 are arranged to image the front surfaces of the teeth 140 and gums (not shown). In accordance with another embodiment of the present invention, the optical fiber layer 720 and the sensor layer 730 may be reversed such that the inner surfaces of the patient's cheeks (buccal surfaces) and lips may be imaged.

The configuration 700 further includes a plurality of illumination sources 740 interspersed across the optical fiber layer 720. The illumination sources 740 may include LEDs, laser diodes, or LEDs or laser diodes coupled to at least one optical fiber. The configuration also includes an electronic cable 750 operatively coupled to the sensor layer 730. The electronic cable 750 provides a transmission path for transmitting digital image data formed by the sensor layer 730 out of the sensor layer 730. The configuration 700 further includes a hollow bite piece 760 mechanically attached to at least one of the sensor layer 730 and the optical fiber layer 720, and having the electronic cable 750 positioned therethrough. The electronic cable 750 may also provide a transmission path for control signals from an image processor and/or an image acquisition machine in order to trigger the sensor layer 730 to acquire image data.

Figure 8:
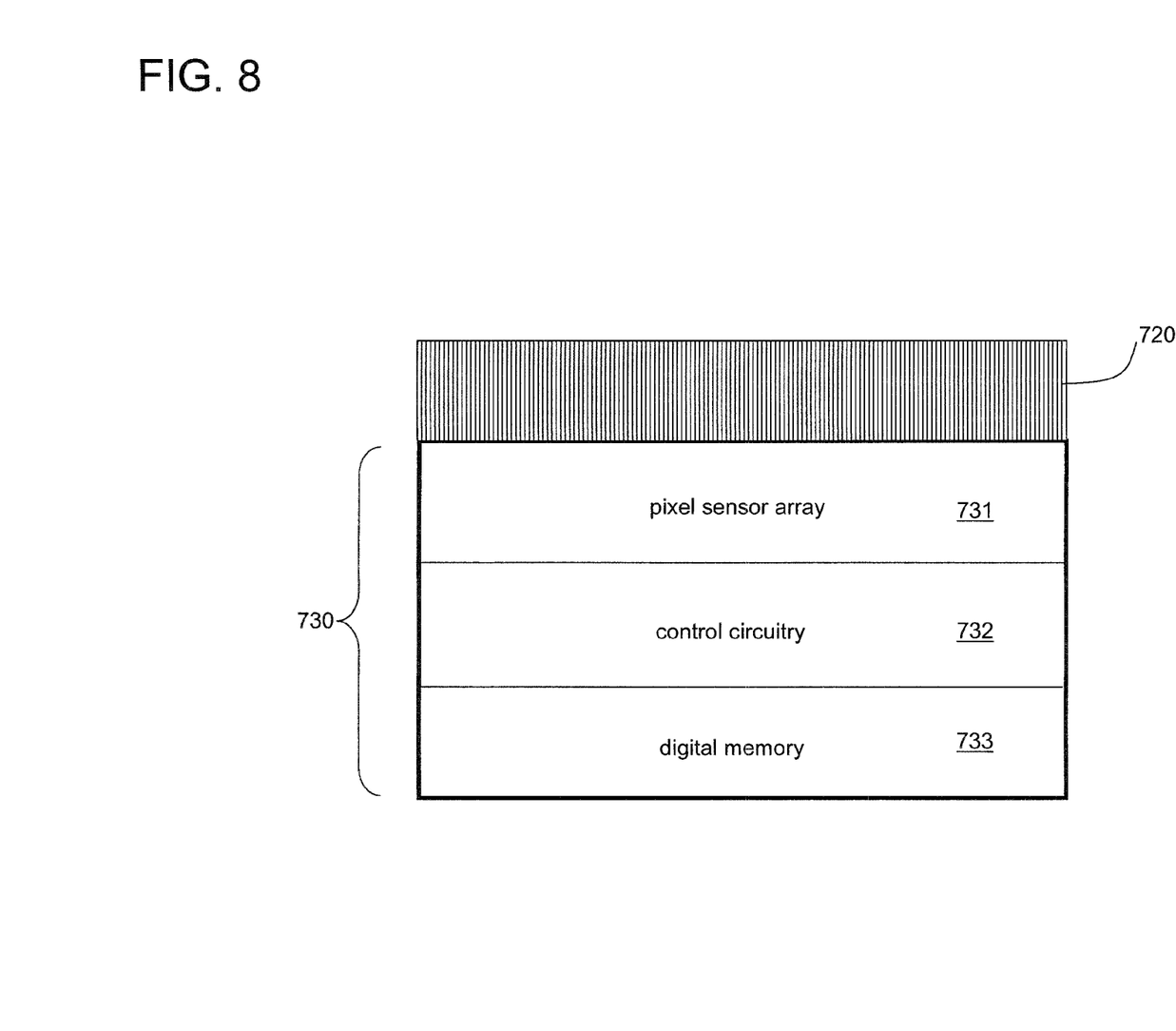
FIG. 8 illustrates a schematic block diagram of a portion of a cross section of the layered structure of FIG. 7.

FIG. 8 illustrates a schematic block diagram of a portion of a cross section of the layered structure 710. The sensor layer 730 includes a pixel sensor array 731 capable of converting the captured electromagnetic energy to electrical signals. The pixel sensor array 732 may be a part of a CCD, a solid state device, an active pixel sensor array, a CMOS array, or any other type of device capable of converting electromagnetic energy to form a plurality of pixels of representative electrical signals, as are well known in the art, in accordance with various embodiments of the present invention.

The sensor layer 730 also includes a digital memory 733 and control circuitry 732 capable of reading out the electrical signals from the pixel sensor array 731 and storing a representation of the electrical signals to the digital memory 733 as pixels of digital image data. The control circuitry 732 is also capable of reading out the digital image data from the digital memory 733 and transmitting the digital image data over the electronic cable 750. An external power source (not shown) provides electrical power to the sensor layer 730 via the electronic cable 750.

As an alternative, the sensor layer 730 may include a pixel sensor array 731 capable of converting the captured electromagnetic energy to electrical signals, and control circuitry 732 capable of reading out the electrical signals as digital image data directly from the pixel sensor array 731 and transmitting the digital image data over the electronic cable 750. In accordance with certain embodiments of the present invention, the control circuitry 732 is capable of reading out and transmitting the digital image data in one of a serial manner, a parallel manner, or some segmented combination thereof.

The configuration 700 also includes an electrical connector 770 operatively coupled at a proximal end of the electronic cable 750. The electrical connector 770 may allow the cable 750 to operatively interface to an image processor and/or an image acquisition machine, for example, in order to acquire intraoral images and process and display those images. As an alternative, the configuration 700 may include an RF antenna (e.g., as shown in FIG. 2) operatively coupled at a proximal end of the electronic cable 750. The RF antenna may allow the configuration 700 to wirelessly interface to an image processor and/or an image acquisition machine, for example, in order to acquire intraoral images and process and display those images.

The layered structure 710 may be alternately configured to image occlusion portions (e.g., 141) of the teeth 140, for example. In such a configuration, the patient bites down lightly on the layered structure to image top and/or bottom occlusion portions of the teeth 140. In such a configuration, the layered structure is oriented within the patient's mouth such that the layered structure has a vertically stacked construction as opposed to the horizontally stacked construction of FIG. 7. For example, the configuration may be placed inside the patient's mouth in a first upright orientation to image the occlusion portions of the top teeth. Subsequently, the configuration may be placed upside down in the patient's mouth to image the occlusion portions of the bottom teeth.

A layered structure capable of imaging both top and bottom occlusion portions of teeth essentially at the same time include two outer optical fiber layers and at least two inner pixel sensor arrays, one for each optical fiber layer. The control circuitry and digital memory may be shared by the two pixel sensor arrays, for example. Other layered constructions are possible as well.

Figure 9:
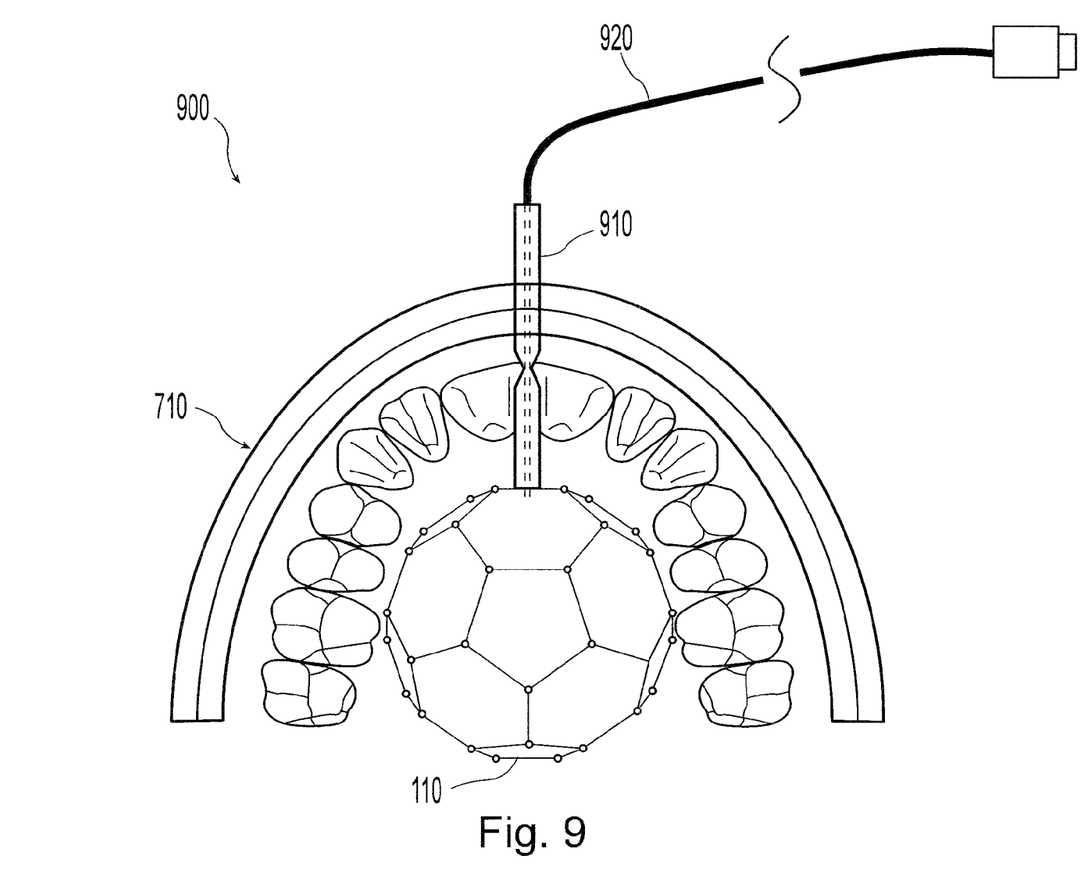
FIG. 9 illustrates a schematic diagram of a fourth exemplary embodiment of an intraoral sensor configuration having the multi-aperture digital camera of FIG. 1 and the conformal layered structure of FIG. 7.

FIG. 9 illustrates a schematic diagram of a fourth exemplary embodiment of an intraoral sensor configuration 900 having the multi-aperture digital camera 110 of FIG. 1 and the conformal layered structure 710 of FIG. 7 in combination. A common bite piece 910, having an electronic cable 920 therethrough, is attached to both the layered structure 710 and the multi-aperture digital camera 110 to hold each in place during imaging. The electronic cable 920 provides a transmission path for digital image data formed by both the conformal layered structure 710 and the multi-aperture digital camera 110. Such a configuration 900 allows imaging of more intraoral portions of the mouth in a single configuration.

Figure 10:
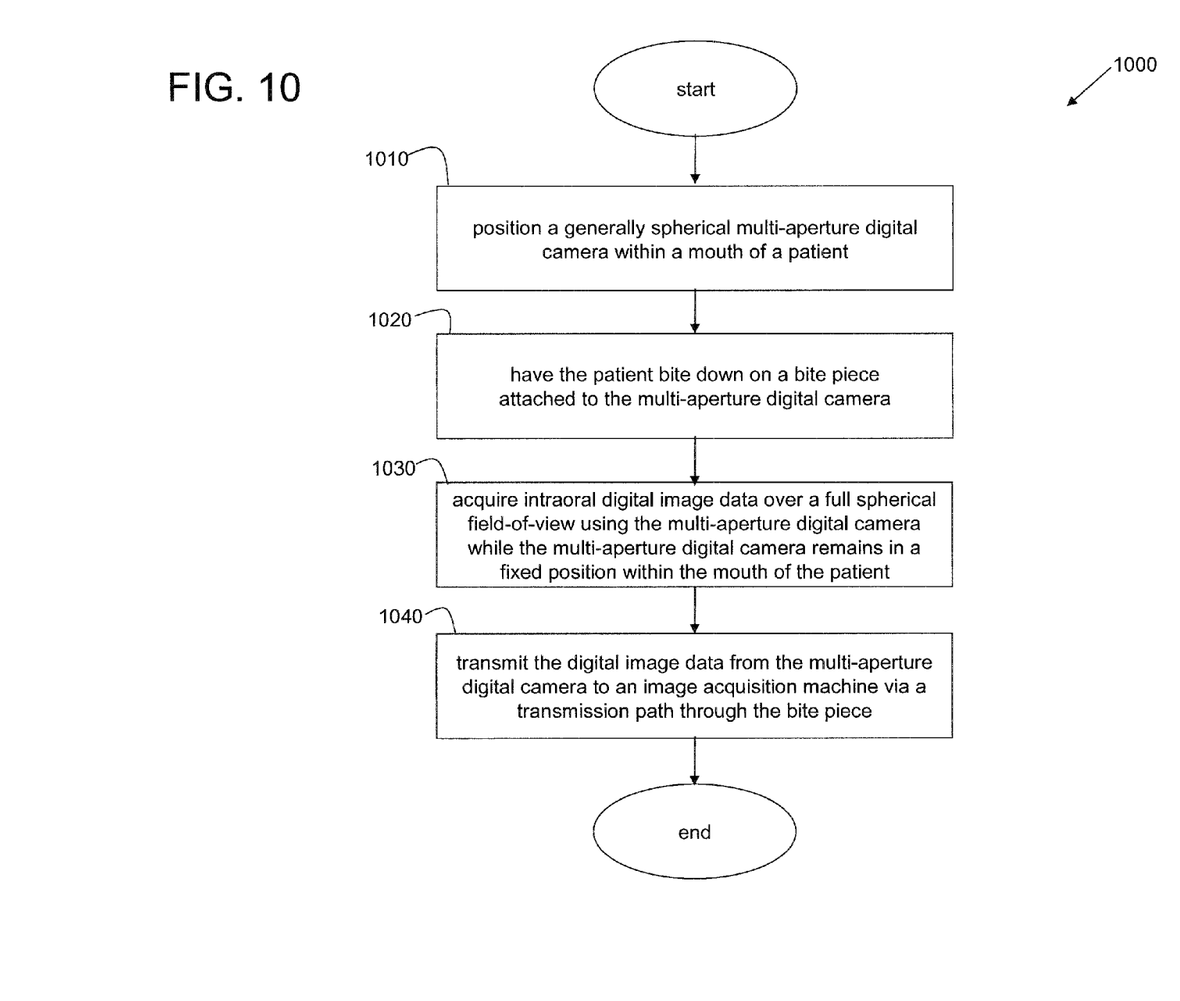
FIG. 10 is a flow chart of a first exemplary embodiment of a method to image inside surfaces within a mouth of a patient.

FIG. 10 is a flow chart of an exemplary embodiment of a method 1000 to image inside surfaces within a mouth of a patient. The method includes, in step 1010, positioning a generally spherical multi-aperture digital camera within a mouth of the patient and, in step 1020, having the patient bite down on a hollow bite piece attached to the multi-aperture digital camera. The method further includes, in step 1030, acquiring intraoral digital image data over a full spherical field-of-view using the multi-aperture digital camera while the multi-aperture digital camera remains in a fixed position within the mouth of the patient. The method also includes, in step 1040, transmitting the digital image data from the multi-aperture digital camera to an image acquisition machine via a transmission path through the hollow bite piece.

Figure 11:
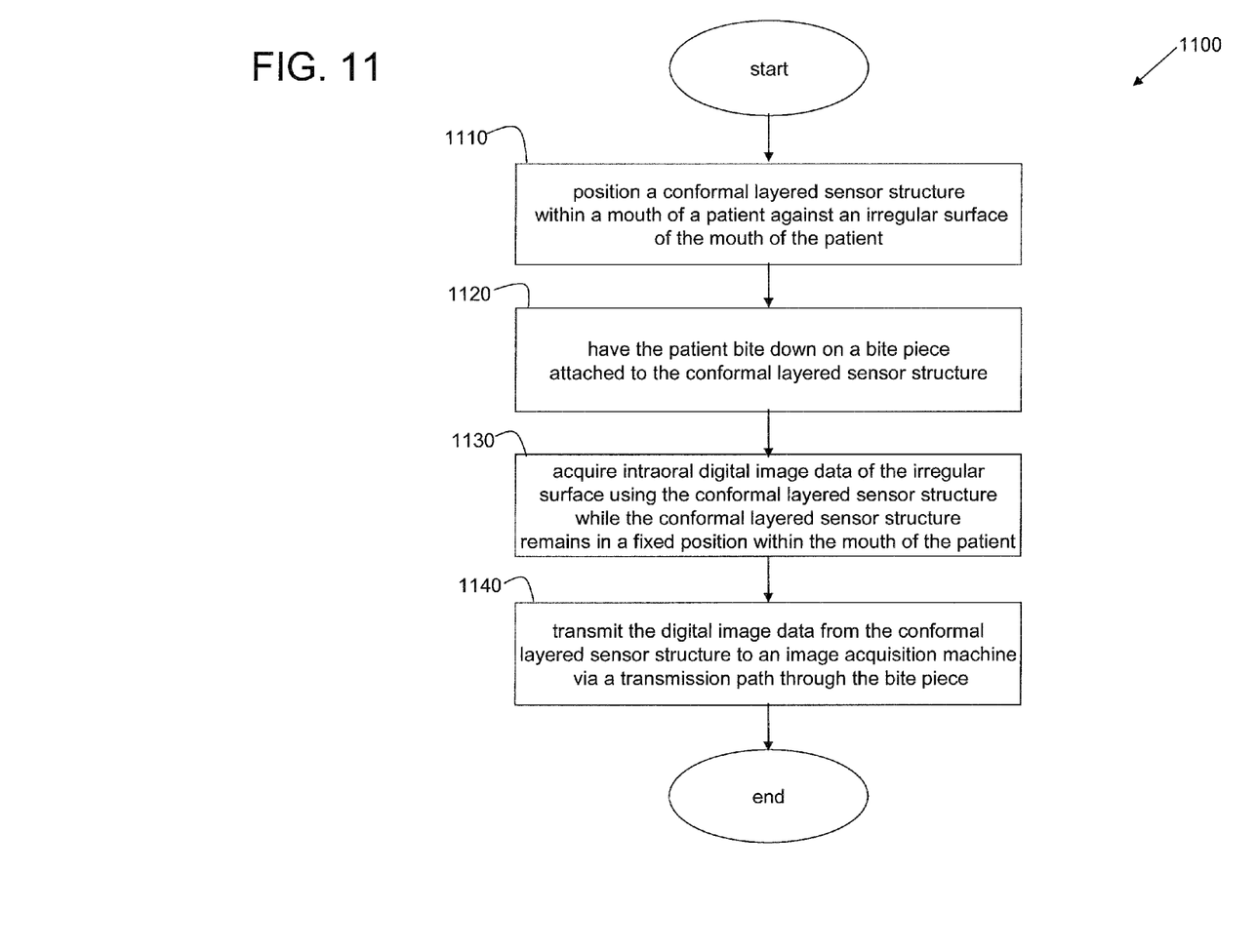
FIG. 11 is a flow chart of a second exemplary embodiment of a method to image inside surfaces within a mouth of a patient.

FIG. 11 is a flow chart of an exemplary embodiment of a method 1100 to image inside surfaces within a mouth of a patient. The method includes, in step 1110, positioning a conformal layered sensor structure within a mouth of a patient against an irregular surface of the mouth of the patient and, in step 1120, having the patient bite down on a hollow bite piece attached to the conformal layered sensor structure. As used herein, the term "irregular surface" means that the surface is at least substantially curved such as, for example, as is the surface along the front portions of the teeth and gums of the patient. The method further includes, in step 1130, acquiring intraoral digital image data of the irregular surface using the conformal layered sensor structure while the conformal layered sensor structure remains in a fixed position within the mouth of the patient. The method also includes, in step 1140, transmitting the digital image data from the conformal layered sensor structure to an image acquisition machine via a transmission path through the hollow bite piece.

When all acquired digital image data is transferred out of the multi-aperture digital camera and/or conformal layered sensor structure, the images may be superimposed onto a three-dimensional (3-D) model in order to provide an accurate 3-D representation of the patient's mouth.

In summary, apparatus and methods for full-mouth intraoral image acquisition are disclosed. An intraoral sensor configuration includes a multi-aperture digital camera and/or a conformal layered sensor structure, a hollow bite piece, and an electronic cable for imaging inside surfaces of a mouth of a patient without having to re-position the digital camera and/or the conformal layered sensor structure within the mouth of the patient during an image acquisition session. Images may be acquired sequentially or simultaneously.

While the claimed subject matter of the present application has been described with reference to certain embodiments, it will be understood by those skilled in the art that various changes may be made and equivalents may be substituted without departing from the scope of the claimed subject matter. In addition, many modifications may be made to adapt a particular situation or material to the teachings of the claimed subject matter without departing from its scope. Therefore, it is intended that the claimed subject matter not be limited to the particular embodiments disclosed, but that the claimed subject matter will include all embodiments falling within the scope of the appended claims.

What is claimed is:

1. An intraoral sensor configuration, said configuration comprising:
   a multi-aperture digital camera having a generally spherical shape and being of a size to fit in a mouth of a patient to image inside surfaces of said mouth of said patient over a generally spherical field-of-view while remaining in a fixed position within said mouth;
   a bite piece attached to said generally spherical multi-aperture digital camera at a distal end of said bite piece; and
   an electronic cable positioned through said bite piece and having a distal end thereof operatively coupled internally to said generally spherical multi-aperture digital camera, said cable providing a transmission path for transmitting digital image data formed by said multi-aperture digital camera out of said multi-aperture digital camera through said bite piece.

2. The intraoral sensor configuration of claim 1 wherein said multi-aperture digital camera comprises:
   a plurality of optical apertures arranged in a generally spherical configuration;
   a plurality of illumination sources arranged between said plurality of optical apertures;
   a plurality of sensor arrays, one sensor array arranged behind each of said optical apertures, capable of capturing electromagnetic energy passing through said optical apertures and converting said captured electromagnetic energy to electrical signals;
   a digital memory;
   first control circuitry capable of reading out said electrical signals from said plurality of sensor arrays and storing a representation of said electrical signals to said digital memory as pixels of said digital image data; and
   second control circuitry capable of reading out said digital image data from said digital memory and transmitting said digital image data over said electronic cable.

3. The intraoral sensor configuration of claim 2 wherein said multi-aperture digital camera further comprises an internal power source capable of providing power to at least one of said plurality of illumination sources, said plurality of sensor arrays, said digital memory, said first control circuitry, and said second control circuitry.

4. The intraoral sensor configuration of claim 3 wherein said internal power source comprises a battery.

5. The intraoral sensor configuration of claim 2 further comprising an external power source capable of providing power to at least one of said plurality of illumination sources, said plurality of sensor arrays, said digital memory, said first control circuitry, and said second control circuitry via said electronic cable.

6. The intraoral sensor configuration of claim 5 wherein said external power source comprises a power supply.

7. The intraoral sensor configuration of claim 2 wherein said second control circuitry is capable of reading out and transmitting said digital image data in a serial manner.

8. The intraoral sensor configuration of claim 2 wherein said second control circuitry is capable of reading out and transmitting said digital image data in a parallel manner.

9. The intraoral sensor configuration of claim 2 wherein said electromagnetic energy comprises at least one of visible light energy, ultraviolet energy, and infrared energy.

10. The intraoral sensor configuration of claim 2 wherein each of said plurality of optical apertures comprises a wide-angle optical lens.

11. The intraoral sensor configuration of claim 2 wherein each of said plurality of optical apertures comprises an optical fiber.

12. The intraoral sensor configuration of claim 2 wherein each of said plurality of optical apertures comprises an optical fiber bundle.

13. The intraoral sensor configuration of claim 2 wherein each of said illumination sources comprises at least one of a light emitting diode, a laser diode, a light emitting diode optically coupled to at least one optical fiber, a laser diode optically coupled to at least one optical fiber.

14. The intraoral sensor configuration of claim 2 wherein each of said plurality of sensor arrays comprises a charge-coupled device (CCD).

15. The intraoral sensor configuration of claim 2 wherein each of said plurality of sensor arrays comprises a solid state device.

16. The intraoral sensor configuration of claim 2 wherein each of said plurality of sensor arrays comprises an active pixel sensor array.

17. The intraoral sensor configuration of claim 2 wherein each of said plurality of sensor arrays comprises a complementary metal oxide semiconductor (CMOS) array.

18. The intraoral sensor configuration of claim 2 wherein, during an image acquisition process, said plurality of sensor arrays are capable of capturing electromagnetic energy one sensor array at a time.

19. The intraoral sensor configuration of claim 2 wherein, during an image acquisition process, said plurality of sensor arrays are capable of capturing electromagnetic energy at the same time.

20. The intraoral sensor configuration of claim 1 further comprising an electrical connector operatively coupled at a proximal end of said electronic cable.

21. The intraoral sensor configuration of claim 1 further comprising a radio frequency antenna operatively coupled at a proximal end of said electronic cable.

22. The intraoral sensor configuration of claim 1 wherein said cable further provides a transmission path for transmitting control signals from an image processor to said multi-aperture digital camera through said bite piece.

23. The intraoral sensor configuration of claim 1 wherein said multi-aperture digital camera comprises:
- a plurality of optical apertures arranged in a generally spherical configuration;
- a plurality of illumination sources arranged between said plurality of optical apertures;
- a single movable sensor array, movably mounted within said generally spherical configuration of optical apertures, capable of capturing electromagnetic energy passing through said optical apertures and converting said captured electromagnetic energy to electrical signals as said single movable sensor array moves;
- a digital memory;
- first control circuitry capable of reading out said electrical signals from said single movable sensor array and storing a representation of said electrical signals to said digital memory as pixels of said digital image data; and
- second control circuitry capable of reading out said digital image data from said digital memory and transmitting said digital image data over said electronic cable.

24. An intraoral sensor configuration, said configuration comprising:
- a multi-aperture digital camera having a generally spherical shape and being of a size to fit in a mouth of a patient to image inside surfaces of said mouth of said patient over a generally spherical field-of-view while remaining in a fixed position within said mouth;
- a bite piece attached to said generally spherical multi-aperture digital camera at a distal end of said bite piece;
- a layered structure of at least optical fibers and pixel sensor arrays attached to said bite piece at a generally middle portion of said bite piece and having a conformal shape to image at least one of buccal surfaces of said mouth, occlusion surfaces of teeth within said mouth, and frontal surfaces of teeth within said mouth while remaining in a fixed position within said mouth; and
- at least one electronic cable positioned through said bite piece and being operatively coupled internally to said generally spherical multi-aperture digital camera and said layered structure, said at least one cable providing a transmission path for transmitting digital image data formed by said multi-aperture digital camera and said layered structure out of said multi-aperture digital camera and said layered structure through said bite piece.

25. A method to image inside surfaces within a mouth of a patient, said method comprising:
- positioning a generally spherical multi-aperture digital camera within a mouth of a patient;
- said patient biting down on a bite piece attached to said multi-aperture digital camera;
- acquiring intraoral digital image data over a full spherical field-of-view using said multi-aperture digital camera while said multi-aperture digital camera remains in a fixed position within said mouth of said patient; and
- transmitting said digital image data from said multi-aperture digital camera to an image acquisition machine via a transmission path through said bite piece.

* * * * *